US00PP16312P2

(12) United States Plant Patent
Dupont, Jr.

(10) Patent No.: US PP16,312 P2
(45) Date of Patent: Mar. 7, 2006

(54) ***SCAEVOLA* PLANT NAMED 'CAJUN BLUE'**

(50) Latin Name: *Scaevola aemula*
Varietal Denomination: Cajun Blue

(75) Inventor: Robert J. Dupont, Jr., Plaquemine, LA (US)

(73) Assignee: Dupont Nursery, Inc., Plaquemine, LA (US)

( * ) Notice: Subject to any disclaimer, the term of this patent is extended or adjusted under 35 U.S.C. 154(b) by 35 days.

(21) Appl. No.: 11/041,618

(22) Filed: Jan. 22, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Scaevola* plant named Cajun Blue, characterized by its compact and trailing plant habit; freely branching habit; dense and bushy plant form; freely and early flowering habit; long flowering period; and blue violet-colored flowers.

2 Drawing Sheets

Botanical designation: *Scaevola aemula.*
Cultivar denomination: 'Cajun blue'.

BACKGROUND OF THE INVENTION

The present Invention relates to a new and distinct cultivar of *Scaevola* plant, botanically known as *Scaevola aemula* and hereinafter referred to by the cultivar name 'Cajun Blue'.

The new *Scaevola* is a product of a planned breeding program conducted by the Inventor in Plaquemine, La. The new *Scaevola* originated from a cross-pollination made by the Inventor in July, 2001, of the *Scaevola aemula* cultivar Blue Wonder, disclosed in U.S. Plant Pat. No. 7,929, as the female, or seed, parent with the *Scaevola aemula* cultivar Oro Blue, not patented, as the male, or pollen, parent. The new *Scaevola* was discovered and selected by the Inventor in August, 2001 in a controlled environment in Plaquemine, La. as a single flowering plant within the resulting progeny from the stated cross-pollination.

Asexual reproduction of the new cultivar by terminal cuttings at Plaquemine, La. since September, 2001, has shown that the unique features of this new *Scaevola* are stable and reproduced true to type in successive generations.

SUMMARY OF THE INVENTION

The new cultivar has not been observed under all possible environmental conditions. The phenotype may vary somewhat with variations in environment such as temperature and light intensity, without, however, any variance in genotype.

The following characteristics have been repeatedly observed and are determined to be the basic characteristics of 'Cajun Blue' which distinguish 'Cajun Blue' as a new and distinct cultivar:

1. Compact and trailing plant habit.
2. Freely branching habit; dense and bushy plant form.
3. Freely and early flowering habit.
4. Long flowering period.
5. Blue violet-colored flowers.

Plants of the new *Scaevola* can be compared to plants of the female parent, the cultivar Blue Wonder. In side-by-side comparisons conducted by the Inventor in Plaquemine, La., plants of the new *Scaevola* and the cultivar Blue Wonder differed in the following characteristics:

1. Plants of the new *Scaevola* were more compact than plants of the cultivar Blue Wonder.
2. Plants of the new *Scaevola* had a more trailing plant habit than plants of the cultivar Blue Wonder.
3. Plants of the new *Scaevola* flowered earlier than plants of the cultivar Blue Wonder.
4. Plants of the new *Scaevola* had larger flower clusters than plants of the cultivar Blue Wonder.

Plants of the new *Scaevola* can be compared to plants of the male parent, the cultivar Oro Blue. In side-by-side comparisons conducted by the Inventor in Plaquemine, La., plants of the new *Scaevola* and the cultivar Oro Blue differed in the following characteristics:

1. Plants of the new *Scaevola* were more compact and more uniform in plant habit than plants of the cultivar Oro Blue.
2. Plants of the new *Scaevola* flowered earlier than plants of the cultivar Oro Blue.

Plants of the new *Scaevola* can be compared to plants of the *Scaevola* cultivar Newon, disclosed in U.S. Plant Pat. No. 10,584. In side-by-side comparisons conducted in north central Texas, plants of the new *Scaevola* differed from plants of the cultivar Newon in the following characteristics:

1. Plants of the new *Scaevola* had longer internodes than plants of the cultivar Newon.
2. Plants of the new *Scaevola* had more serrated leaves than plants of the cultivar Newon.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Scaevola*.

The photograph on the first sheet comprises a side perspective view of a typical plant of 'Cajun Blue' grown in a hanging basket container.

The photograph at the top of the sheet is a close-up view of typical leaves and flowers of 'Cajun Blue'.

DETAILED BOTANICAL DESCRIPTION

Plants used in the aforementioned photographs and for the following description were grown under conditions which closely approximate commercial production conditions during the spring and summer in a polyethylene-covered greenhouse in Plaquemine, La. Plants were about four months from planting rooted cuttings. In the following description, color references are made to The Royal Horticultural Society Colour Chart, 1995 Edition, except where general terms of ordinary dictionary significance are used.

Botanical classification: *Scaevola aemula* cultivar Cajun Blue.

Parentage:

*Female parent.*—*Scaevola aemula* cultivar Blue Wonder, disclosed in U.S. Plant Pat. No. 7,929.

*Male parent.*—*Scaevola aemula* cultivar Oro Blue, not patented.

Propagation:

*Type cutting.*—Terminal cuttings.

*Time to develop roots.*—About four weeks at 22° C.

*Root description/habit.*—Fine, fibrous and freely branching.

Plant description:

*Plant form and growth habit.*—Annual container and garden plant. Compact and trailing plant habit; plants eventually become roughly spherical in shape. Freely branching with lateral branches potentially forming at every vegetative leaf axil when pinched; dense and bushy plant form. Moderately vigorous growth habit.

*Plant height* (*soil level to top of plant plane*).—About 16 to 20 cm.

*Plant diameter.*—About 48 cm.

*Lateral branch description.*—Length: About 25 cm. Diameter: About 2.5 mm. Internode length: About 2 to 4 cm. Texture: Smooth, glabrous. Color: 144A to 146A.

*Foliage description.*—Arrangement: Alternate, simple; sessile. Length: About 4 to 6 cm. Width: About 1.5 to 3 cm. Shape: Oblanceolate. Apex: Rounded to acute. Base: Attenuate. Margin: Irregularly serrated. Texture, upper and lower surfaces: Slightly pubescent; somewhat leathery. Venation pattern: Pinnate. Color: Developing and fully expanded leaves, upper surface: 147A. Developing and fully expanded leaves, lower surface: 147B. Venation, upper surface: 147A. Venation, lower surface: Close to 147B to slightly darker than 144A.

Flower description:

*Flower type and shape.*—Zygomorphic, semi-circular, fan-shaped flowers with five petals fused at the base to form a tubular flower throat. Flower throat open along the upper surface exposing reproductive organs. Flowers not persistent. No fragrance detected.

*Flower arrangement and quantity.*—Solitary flowers arise from leaf axils with one flower per axil. Flowers held outwardly on upturned lateral apices. Freely flowering, typically about ten open flowers per inflorescence.

*Flowering time.*—Early flowering habit and long flowering period; plants flower continuously from May until frost in Plaquemine, La. Flowers typically last about one to two weeks on the plant.

*Flower buds.*—Shape: Lanceolate. Length: About 1 cm. Diameter: About 2 mm. Color: 144B overlain with 187C.

*Perianth.*—Aspect: Fan-shaped, flat. Length, fan: About 2.1 cm. Width, fan: About 3 cm. Flower throat diameter: About 7.5 mm. Flower tube length: About 1.2 cm. Flower tube diameter, base: About 2 mm.

*Petals.*—Quantity: Five, fused at base. Shape: Lanceolate. Apex: Cuspidate. Margin: Entire. Length, above tube: About 1.3 cm. Width, above tube: About 5.7 mm. Texture, upper and lower surfaces: Smooth, glabrous; flower throat, whiskered. Color: When opening, upper surface: Close to 90B. When opening, lower surface and tube: Close to 90B. Fully opened, upper surface: 90B to 90C; color becoming closer to 90C to lighter than 90D with development; towards the base, close to 155D. Fully opened, lower surface: 90C to 90D. Throat: 5A. Tube: Close to 145C.

*Sepals.*—Quantity and arrangement: One large sepal, two smaller sepals lateral to larger sepal. Length: Larger sepal, about 1.2 cm; lateral sepals, about 5 mm. Width: Larger sepal, about 7 mm; lateral sepals, about 1 mm. Shape: Larger sepal, roughly ovate; lateral sepals, acicular, needle-like. Apex: Acute. Margin: Entire. Texture, upper and lower surfaces: Slightly pubescent. Color, upper surface: 147A. Color, lower surface: 147B.

*Reproductive organs.*—Androecium: Stamen quantity per flower: About five. Anthers: Shape: Ovate. Length: About 1.5 mm. Diameter: About 1 mm. Color: 20C. Filament length: About 4 mm. Pollen: Sparse. Pollen color: Close to 20C. Gynoecium: Pistil quantity per flower: One. Pistil length: About 1.25 cm. Style length: About 7.5 mm. Style color: Towards the base, 145D; towards the apex, 187A. Stigma shape: Elongate. Stigma color: Close to 155A. Ovary color: 144A.

*Seed/fruit.*—Seed and fruit production has not been observed.

Disease/pest resistance: Plants of the new *Scaevola* have not been noted to be resistant to pathogens and pests common to *Scaevola*.

Temperature tolerance: Plants of the new *Scaevola* have been observed to be tolerant to temperatures ranging from 2 to 30° C.

It is claimed:

1. A new and distinct *Scaevola* plant named Cajun Blue, as illustrated and described.

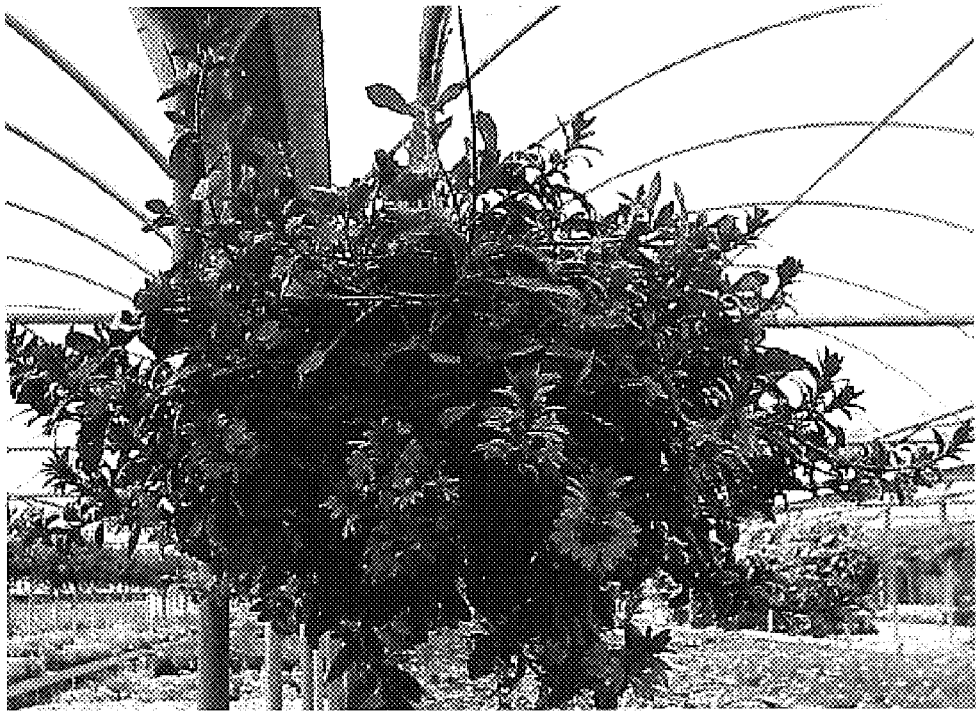

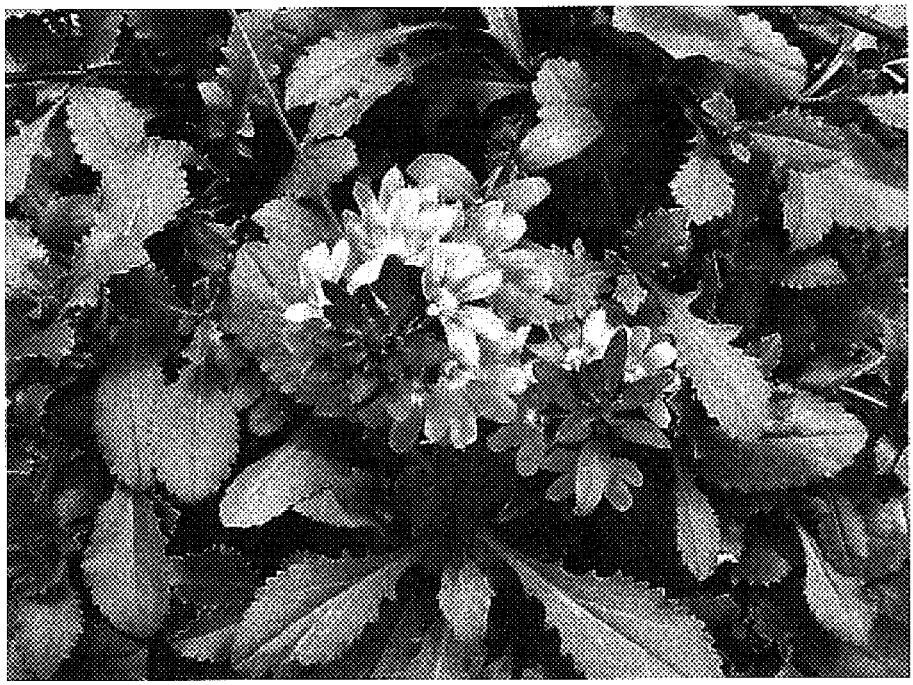

* * * * *